(12) United States Patent
Shroff et al.

(10) Patent No.: US 9,370,179 B2
(45) Date of Patent: *Jun. 21, 2016

(54) STABLE ENCAPSULATED FORMULATION OF CLOMAZONE

(71) Applicants: Jaidev Rajnikant Shroff, Mumbai (IN); Vikram Rajnikant Shroff, Mumbai (IN); Prakash Mahadev Jadhav, Mumbai (IN); Christian Becker, King of Prussia, PA (US)

(72) Inventors: Jaidev Rajnikant Shroff, Mumbai (IN); Vikram Rajnikant Shroff, Mumbai (IN); Prakash Mahadev Jadhav, Mumbai (IN); Christian Becker, King of Prussia, PA (US)

(73) Assignee: UPL Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/674,202

(22) Filed: Mar. 31, 2015

(65) Prior Publication Data

US 2015/0201614 A1 Jul. 23, 2015

Related U.S. Application Data

(63) Continuation of application No. 13/582,984, filed as application No. PCT/IB2011/000543 on Mar. 15, 2011, now Pat. No. 9,034,795.

(30) Foreign Application Priority Data

Mar. 29, 2010 (IN) .......................... 902/MUM/2010

(51) Int. Cl.
*A01N 25/34* (2006.01)
*A01N 43/80* (2006.01)

(52) U.S. Cl.
CPC ............... *A01N 25/34* (2013.01); *A01N 43/80* (2013.01)

(58) Field of Classification Search
None
See application file for complete search history.

(56) References Cited

U.S. PATENT DOCUMENTS 3,592,910 A * 7/1971 Clark et al. ................... 514/481
5,583,090 A * 12/1996 Stern et al. ................... 504/140

FOREIGN PATENT DOCUMENTS

| CN | 101606517 | 12/2009 |
|----|-----------|---------|
| WO | 96/14743 | 5/1996 |
| WO | 98/24317 | 6/1998 |

* cited by examiner

*Primary Examiner* — Michael B Pallay
(74) *Attorney, Agent, or Firm* — Yancy IP Law, PLLC

(57) ABSTRACT

A storage stable capsule suspension formulation comprising clomazone encapsulated within a polymeric shell wall of microcapsules, a process for the preparation thereof and method of controlling weeds utilizing said formulation.

15 Claims, No Drawings

STABLE ENCAPSULATED FORMULATION OF CLOMAZONE

FIELD OF THE INVENTION

The present invention relates to an agrochemical formulation comprising encapsulated clomazone. More particularly, the present invention relates to a non-volatile agrochemical formulation comprising encapsulated clomazone.

BACKGROUND OF THE INVENTION

Clomazone is the common name for the herbicide 2-(2-chlorophenyl)methyl-4,4-dimethyl-3-isoxazolinone. It is a colorless to light brown and viscous liquid above room temperature, which forms a white crystalline solid when cooled. It is not flammable in nature.

Clomazone has the following chemical structure:

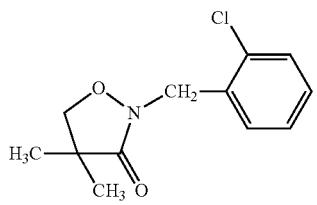 [SMILES: CC1(C)CON(Cc2ccccc2Cl)C1=O]

Clomazone is a highly effective herbicide, but unfortunately is also highly volatile. The amount of clomazone applied to the soil in a target area may move to adjacent areas and cause discoloration. This discoloration is typically in the form of whitening or some degree of bleaching, of a variety of crops, trees, or decorative plants. This bleaching, which is also indicative of the mode of action of the herbicide, may be temporary when plants are exposed to sufficiently low concentrations. However, bleaching of the crops, trees or decorative plants is undesirable even when it does not result in the destruction of the plant.

Clomazone is a broad spectrum herbicide used for control of annual grasses and broadleaf weeds in cotton, peas, pumpkins, vegetables, sweet potatoes, tobacco, winter squash and fallow wheat fields. It can be applied early preplant, preemergent or preplant-incorporated depending on the crop, geographical area and timing. Because clomazone is an inhibitor of plant pigments, users must exercise caution to avoid drift or vapors which may cause bleaching damage to non-target foliage.

Clomazone is relatively stable to degradation by UV light. It is highly volatile and can drift during or after application, causing damage to sensitive, non-target plants such as ornamental trees and shrubs, roses, small grains, alfalfa, sunflowers, and vegetable crops. Clomazone is slightly soluble in water, but it has a moderate tendency to adsorb to soil particles. It therefore has a low to moderate potential to contaminate groundwater.

Hitherto, a non-encapsulated emulsifiable concentrated formulation of clomazone has been available. However, upon application of the conventional emulsifiable concentrated formulation, the sensitive plants surrounding the intended targets of application displayed varying degrees of whitening due to the high volatility of clomazone. Thus, an encapsulated formulation of clomazone was desirable which was believed to be capable of reducing the volatility of clomazone and improve the active component delivery to the targeted plants.

Attempts to prepare formulations of encapsulated clomazone by encapsulating clomazone in polyurea and polyamide polymeric shells frequently resulted in formulations that not only gave little or no reduction in volatility, but had poor physical characteristics such as undesirable agglomeration of the capsules or separation of phases or breaking of the capsule wall on spray application which results into failure to achieve the volatility reduction. It was thus desirable to provide a herbicidal formulation having an improved plasticity of the polymeric shell wall to reach an acceptable release rate of the active ingredient clomazone. It is believed that an improvement in plasticity of the polymeric shell wall would substantially reduce the permeation of the shell wall to the active ingredient and possibly limit the breakage of the capsule wall on spray application, which would consequently achieve a substantial reduction in volatility of the formulation.

Another challenge during the encapsulation of clomazone had been its relatively higher water solubility. The known encapsulation methods involve a reaction between an aqueous phase and an organic phase. It was found that the low/mild solubility of clomazone in water did result into poorly defined droplets and also increased the amount of the free active ingredient in the aqueous phase. An increased amount of clomazone in the aqueous phase could contribute to an increased initial "burst effect" administration of clomazone thereby aggravating the risk of plant phytotoxicity and off-target injury due to the volatility of the free clomazone.

U.S. Pat. No. 5,583,090 is directed to a sprayable herbicidal formulation comprising an aqueous liquid having suspended therein a multitude of solid microcapsules having a capsule wall of a porous polymer encapsulating clomazone dissolved in a high boiling inert organic solvent.

U.S. Pat. No. 5,597,780 teaches a process for preparing herbicidally effective formulations of clomazone by microencapsulating clomazone by interfacial polymerization reaction between an aqueous phase and an organic phase. The organic phase essentially comprises a hydrocarbon solvent.

These patents disclose that when the formulations taught therein are sprayed onto one plot containing vegetation, vapor transfer of the herbicide to a nearby plot containing vegetation is effectively suppressed without substantial sacrifice of herbicidal efficacy of the herbicide in the plot to which the spray is applied. However, the problem of reducing the permeability of the polymeric shell wall to the active ingredient consequently limiting the rupture of the capsule wall on spray application and substantially reducing the volatility of the microencapsulated formulation of clomazone still remains a problem. Further, this problem continues to remain irrespective of the chemical nature of the polymeric shell wall such as a polyamide, polyurea, polyurethane, polycarbonate, melamine resin, melamine urea resin, gelatine/gum arabic or cross linked or non-crosslinked combinations thereof.

There is a further need in the art for a microencapsulated formulation of clomazone that is storage stable and capable of being diluted at the time of application as per requirements. These and other needs of the art are met by a microencapsulated formulation of clomazone described hereinafter.

OBJECTS OF THE INVENTION

The present invention described hereinafter achieves at least one or more of the following objects of the invention.

Accordingly, it is an object of the present invention to provide a storage stable composition comprising encapsulated clomazone.

Another object of the present invention is to provide a formulation of microencapsulated clomazone having reduced volatility thereby substantially reducing the unintended incidences of off-site injury.

Another object of the present invention is to provide a herbicidal formulation comprising a herbicidally effective amount of microencapsulated clomazone that exhibits significant bioefficacy for the control of undesired weeds.

Another object of the present invention is to provide a herbicidal formulation comprising microencapsulated clomazone, wherein said microcapsules containing clomazone possess a high shell wall plasticity and are thus resistant to shell wall breakage.

Another object of the present invention is to provide a herbicidal formulation comprising microencapsulated clomazone which maintains its bioefficacy throughout its shelf life.

Another object of the present invention is to provide a method for substantially reducing the off target vapor transfer of microencapsulated clomazone formulation.

These and other objects of the present invention are realized by way of the practice of the invention described hereinafter.

SUMMARY OF THE INVENTION

Thus, in this aspect, the present invention provides a storage stable capsule suspension formulation comprising a herbicidally effective amount of clomazone encapsulated within a polymeric shell wall of microcapsules, said microcapsules characterized in comprising a stabilizing effective amount of at least one adjuvant selected from epoxidized derivatives of fatty acids or esters thereof and polymers and copolymers of terpenes.

A capsule suspension formulation of clomazone comprising a herbicidally effective amount of microencapsulated clomazone, said microcapsules comprising said herbicidally effective amount of clomazone encapsulated within a polymeric wall, said polymeric wall being formed by an interfacial polymerization reaction occurring between an organic phase dispersed in an aqueous phase, said organic phase being characterized in comprising a stabilizing effective amount of at least one adjuvant selected from epoxidized derivatives of fatty acids or esters thereof and polymers and copolymers of terpenes.

A process for the preparation of a capsule suspension formulation, said process comprising:
  (a) forming an aqueous solution comprising at least one surfactant;
  (b) forming an organic phase by adding a herbicidally effective amount of clomazone to a stabilizing effective amount of at least one adjuvant selected from epoxidized derivatives of fatty acids or esters thereof and polymers and copolymers of terpenes and adding a first wall forming component to said organic phase;
  (c) dispersing said organic phase in said aqueous solution to obtain an emulsion; and
  (d) adding a second wall forming component to said aqueous phase and allowing said second wall forming component to react with said first wall forming component comprised within said emulsion to form a polymeric wall encapsulating said herbicidally effective amount of clomazone.

A method for controlling weeds at a locus comprising applying to the locus of the weeds a herbicidally effective amount of an encapsulated clomazone according to the present invention or a capsule suspension formulation obtainable by the process of the present invention.

DETAILED DESCRIPTION OF THE INVENTION

It has been surprisingly found that the presence of a stabilizing effective amount of at least one adjuvant selected from epoxidized derivatives of fatty acids or esters thereof and polymers and copolymers of terpenes reduces the volatility of an encapsulated clomazone formulation. It has further been found that the presence of at least one such adjuvant surprisingly improves the plasticity of the polymeric shell wall thereby substantially reducing the permeation of the shell wall to the active ingredient. Without wishing to be bound by theory, it has been found that a substantial reduction in the permeation of the shell wall to the active ingredient substantially reduces the volatility of an encapsulated clomazone formulation. The reduction of volatility of clomazone has not been hitherto achieved substantively although a multitude of conventional formulations have attempted to do so.

Accordingly, in one aspect, the present invention provides a storage stable capsule suspension formulation comprising a herbicidally effective amount of clomazone encapsulated within a polymeric shell wall of microcapsules, said microcapsules characterized in comprising a stabilizing effective amount of at least one adjuvant selected from epoxidized derivatives of fatty acids or esters thereof and polymers and copolymers of terpenes.

In an embodiment, a preferred adjuvant is selected from an epoxidized oleochemical and low molecular weight polymers and copolymers of terpenes. Preferably, an epoxidized oleochemical is selected from epoxidized soybean oil and epoxidized linseed oil although other epoxidized vegetable oils are not excluded.

Preferably, the low molecular weight terpenes includes pinene polymers and homopolymers and copolymers thereof. Still more preferably, the preferred pinene polymers are $\alpha$- and $\beta$-pinene copolymers and/or Piccolyte AO. Preferably, the aforesaid $\alpha$- and $\beta$-pinene copolymers are manufactured by various processes that include formation of a dimer, trimer or a polymer of $\alpha$- and $\beta$-pinene.

Thus, in another aspect, the present invention provides a storage stable capsule suspension formulation comprising a herbicidally effective amount of clomazone encapsulated within a polymeric shell wall of microcapsules, said microcapsules characterized in comprising a stabilizing effective amount of at least one adjuvant selected from epoxidized derivatives of fatty acids or esters thereof and polymers and copolymers of terpenes; and at least one further component selected from a plasticizer, a tackifier or a film forming agent.

In another aspect, the present invention provides a capsule suspension formulation of clomazone comprising a herbicidally effective amount of microencapsulated clomazone, said microcapsules comprising said herbicidally effective amount of clomazone encapsulated within a polymeric wall, said polymeric wall being formed by an interfacial polymerization reaction occurring between an organic phase dispersed in an aqueous phase, said organic phase being characterized in comprising a stabilizing effective amount of at least one adjuvant selected from epoxidized derivatives of fatty acids or esters thereof and polymers and copolymers of terpenes.

However, it should be understood that the presence of said aqueous and organic phases for interfacial polymerization are not particularly limiting. The interfacial polymerization reactions suitable for encapsulated formulations according to the present invention may be prepared by reaction between the wall forming components present in two substantially immiscible liquids, of which said organic and aqueous phases constitute a preferred embodiment. Moreover, the two walls forming components may be either same or different or these same or different wall forming components may be comprised within the first phase only or in the second phase only or distributed between said first and second immiscible phases.

In another aspect, the present invention provides a process for the preparation of a capsule suspension formulation, said process comprising:
(a) forming an aqueous solution comprising at least one surfactant;
(b) forming an organic phase by adding a herbicidally effective amount of clomazone to a stabilizing effective amount of at least one adjuvant selected from epoxidized derivatives of fatty acids or esters thereof and polymers and copolymers of terpenes and adding a first wall forming component to said organic phase;
(c) dispersing said organic phase in said aqueous solution to obtain an emulsion; and
(d) adding a second wall forming component to said emulsion and allowing said second wall forming component to react with said first wall forming component comprised within said emulsion to form a polymeric wall encapsulating said herbicidally effective amount of clomazone.

The capsule polymeric wall of the present invention may be any known shell wall material and is preferably selected from a polyurea, a polyurethane, a polyamide, a polycarbonate, a polysulfonamide, a urea formaldehyde, a melamine formaldehyde resin, a melamine urea resin, a gelatine/gum arabic shell wall or crosslinked or non-crosslinked combinations thereof. Preferably, the capsule polymeric wall is a polyurea wall.

In an embodiment, dispersing said aqueous solution in said organic phase to obtain the emulsion comprises mixing said aqueous solution in the organic phase at high speed agitation in order to obtain an emulsion. Preferably, the emulsion comprises particles between 0.1 microns to 200 microns, preferably between 1 micron and 50 microns and more preferably between 2 microns and 10 microns.

In another embodiment, allowing said wall forming components to react with each other comprises allowing a chemical reaction to occur with or without heat for a predetermined amount of time until complete polymerization occurs. Preferably, complete polymerization of the wall forming components occurs between 15 minutes and 5 hours, preferably between half an hour and 4 hours and more preferably between half an hour and 2 hours.

The interfacial polymerization between the wall forming components can be carried at ambient temperature or at an elevated temperature. Accordingly, the temperature range for the reaction is between 5 C and 90° C., preferably between 10° C. and 70° C. and more preferably between 15° C. and 60° C.

In another embodiment, allowing said wall forming components to react with each other comprises maintaining the emulsion for a sufficient period of time to allow substantial completion of the polymerization reaction between said wall forming components such that the liquid droplets in the organic phase are converted to capsules comprising polyurea shells enclosing clomazone active ingredient.

The capsule polymeric wall of the present invention is formed using interfacial polymerization by contacting said second wall forming component added to the aqueous solution with a first wall forming component present within the organic phase as is conventionally known in the art.

The first wall forming component is preferably selected from a polyisocyanate, a polyacid chloride, a polychloroformate and a polysulfonyl chloride. The second wall forming component is preferably selected from a polyamine and/or polyol. Preferably, a polyisocyanate reacts with a polyamine to form a polyurea capsule wall of the present invention.

The preferred polyisocyanates as the first wall forming component may be selected from tetramethylene diisocyanate, pentamethylene diisocyanate, hexamethylene diisocyanate, toluene diisocyanate, diphenylmethane-4,4'-diisocyanate, polymethylene polyphenylene isocyanate, 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate and 4,4'4"-triphenylmethane triisocyanate. A preferred polyisocyanate first wall forming component is toluene diisocyanate or polymethylene polyphenylisocyanate.

The preferred polyamines as the second wall forming components may be selected from ethylenediamine, propylene-1, 3-diamine, tetramethylenediamine, pentamethylenediamine, 1,6-hexamethylenediamine, diethylenetriamine, triethylenetetramine, tetraethylenepentamine, pentaethylenehexamine, 4,9-dioxadodecane-1,12-diamine, 1,3-phenylenediamine, 2,4- and 2,6-toluenediamine and 4,4'-diaminodiphenylmethane or acid addition salt thereof. The preferred polyamine according to the present invention is selected from ethylenediamine, diethylenetriamine, triethylenetetramine and tetraethylenepentamine.

The first wall forming component present within the organic phase comprises from about 2% to 25% by weight of the organic phase, preferably from 5% to 20% by weight. The second wall forming component present in the aqueous phase represents from 0.3% to 7% by weight of the total weight of the formulation, preferably 1% to 5% by weight.

The relative quantities of the organic and the aqueous phases are not critical for the process of the present invention. Typically, the organic phase may comprise up to about 75% by volume of the total emulsion and comprises discrete droplets of an organic phase dispersed in the aqueous solution.

The droplet size in the emulsion was not found critical to the formulation and process of the present invention but may be found between 0.1 microns to 200 microns, preferably between 1 micron and 50 microns, which may be further adapted using a high shear device to preferably about 2 microns to about 10 microns.

In an embodiment, the wall forming reaction typically runs to completion within the span of a few minutes to a few hours. In a preferred embodiment, the reaction is typically allowed to run for about half an hour till about 2 to 3 hours.

The aqueous solution comprises at least one surfactant. Preferably, the surfactant may be selected from the group comprising ethoxylated lignosulfonic acid salts, lignosulfonic acid salts, oxidized lignins, lignin salts, salts of styrene-maleic anhydride copolymers, polyvinyl alcohol, salts of partial esters of styrene-maleic anhydride copolymers, partial salts of polyacrylic acid and partial salts of polyacrylic acid terpolymers.

Preferably, the surfactant is lignosulfonate of calcium or sodium or mixtures thereof or a modified kraft lignin with a high sulfonic acid group or a combination thereof in any suitable proportion.

Preferably, the surfactant is present in an amount of about 0.5% to about 1.5% by weight of the formulation.

The term "herbicidally effective amount" of clomazone is that quantity of clomazone which when applied in that amount will provide the required control of weeds. The particular amount is dependent upon many factors including, for example, the crop, weeds sought to be controlled and environmental conditions. The selection of the proper quantity of active agent to be applied, however, is within the expertise of one skilled in the art and is not considered particularly limiting.

A stabilizing effective amount of a adjuvant selected from epoxidized derivatives of fatty acids or esters thereof and polymers and copolymers of terpenes is an amount sufficient to substantially increase the plasticity of the encapsulating polymeric shell wall and consequently minimize the volatility of clomazone to produce a storage stable agrochemical composition having a commercially reasonable shelf life of at least about 2 years. For example, a stabilizing effective amount of adjuvant selected from epoxidized derivatives of fatty acids or esters thereof and polymers and copolymers of terpenes can be up to about 70% by weight of the organic phase in the formulation.

The microencapsulated formulations according to the present invention comprise from about 10% to about 50% of clomazone active ingredient.

In a preferred embodiment, the polymeric shell wall according to the present invention constitutes from about 20% by weight to about 40% by weight of the organic phase in the formulation. In another preferred embodiment, the polymeric shell wall constitutes about 31% by total weight of the organic phase in the formulation.

The release rate of clomazone from the encapsulated formulation according to the present invention was found to be dependent on the wall thickness. Unless otherwise indicated, the wall thickness is defined herein as the ratio of the percentage of wall material to the oil phase.

In an embodiment, the amount of polymeric wall of the formulation capsules according to the 10 invention varies from about 2.5% to about 25%. It was found that an optimum rate of release of the active component without substantially increasing the formulation cost would depend on the type of stabilizing agent such as hereinabove described incorporated with the organic phase. Preferably, the amount of polymeric wall of the formulation capsules related to the organic phase would vary between 6% and 20%.

It was found that increasing the amount of polymeric wall of the formulation capsules related to the organic phase substantially reduced the maximum release rate in air. The formulations were prepared using diethylenetriamine as the amine wall component and comprised about 20% epoxidized soybean oil. A formulation "A" having a wall amount of polymeric wall of the formulation capsules related to the organic phase of about 10% while a formulation "B" was prepared with an amount of polymeric wall of the formulation capsules related to the organic phase of about 20%. It was found that the release rate in air (in % of the active ingredient) was strongly dependent upon the amount of polymeric wall of the formulation capsules related to the organic phase.

| Sample No. | Amount of polymeric wall of the formulation capsules related to the organic phase | Release rate in air after 2 hours at 50 C. (in %)* |
| --- | --- | --- |
| 1 | Formulation A: 10% wall | 9.2 |
| 2 | Formulation B: 20% wall | 1.9 |

*Release rate in air at 50° C. compared to the initial amount of active ingredient present in the formulation.

Preferably, the capsule suspension formulations of the present invention comprise an anti-foam in an amount of about 0.01% to about 5% by weight of the formulation. Such suitable anti-foams are conventionally known in the art and are not particularly limiting.

The capsule suspension of the present invention may further include a rheology modifier. The preferred rheology modifier includes xanthan gum and/or clay, which may be present in an amount of about 0.01% to about 1% by weight of the formulation.

The capsule suspension formulation according to the present invention may further be neutralized with a mineral acid to regulate the pH within the desired range. Accordingly, the formulations according to the present invention additionally comprises from about 0.1% to about 10% of a neutralizing acid, which may be a mineral or an organic acid. Preferably, the mineral acid is hydrochloric acid.

In a preferred embodiment, the formulations according to the present invention may additionally comprise a biocide in an amount of from about 0.01% to about 3% by weight of the formulation.

In a most preferred embodiment, said epoxidized fatty ester is an epoxidized oleochemical and more preferably is epoxidized soybean oil. In a further preferred embodiment, the preferred stabilizing agent may be a polymer or a copolymer of terpenes.

Thus, in this embodiment, the present invention provides a process for the preparation of a capsule suspension formulation, said process comprising:

(a) forming an aqueous solution comprising at least one surfactant;

(b) forming an organic phase by adding herbicidally effective amount of clomazone to a stabilizing effective amount of at least one adjuvant selected from epoxidized derivatives of fatty acids or esters thereof and polymers and copolymers of terpenes and adding a first wall forming component to said organic phase;

(c) dispersing said organic phase in said aqueous solution to obtain an emulsion; and (d) adding the second wall forming component to the emulsion and allowing said second wall forming component to react with said first wall forming component comprised within said emulsion to form a polymeric wall encapsulating said herbicidally effective amount of clomazone.

Preferably, said step of forming an aqueous solution comprises adding said surfactant and at least one further component selected from said rheology modifier, said density modifier and said biocide to a quantity of water. In a preferred embodiment, an antifoam is also added to said aqueous solution.

In yet another preferred embodiment, said step of dispersing said organic phase in said aqueous solution to obtain an emulsion is carried out to a desired particle size.

In another preferred embodiment, subsequent to the addition of the organic phase to the aqueous solution, the reaction is allowed to continue for a predetermined time, preferably one to two hours under stirring.

Subsequently, the reaction mixture is neutralized with an inorganic acid, preferably hydrochloric acid. The neutralization is carried out preferably to attain a formulation pH of from about 6 to about 9.

Subsequently, xanthan gum is preferably added under stirring.

In another embodiment, said rheology modifier may not be added to the aqueous solution but may be added just prior or subsequent to the addition of xanthan gum.

In a preferred embodiment, a biocide is added to obtain the target formulation.

In a preferred embodiment, the process of the present invention is carried out at an elevated temperature to enhance the rate of polymeric wall formation. In this embodiment, the process of the present invention is preferably carried out at a temperature of about 5 C to about 90° C., and is more preferably conducted at a temperature of about 10 to about 70° C., and more preferably of about 15 C to about 60 C.

The preferred epoxidized fatty esters according to the present invention may further be selected from epoxidized palm oil, epoxidized rapeseed oil, epoxidized sunflower oil, epoxidized peanut oil, epoxidized cottonseed oil, epoxidized palm kernel oil, epoxidized coconut oil, epoxidized soybean oil, epoxidized olive oil and epoxidized linseed oil. Preferably, epoxidized soybean oil or epoxidized linseed oil may be used. However, it should be understood that the choice of the particular vegetable oil is not particularly limiting.

The preferred polymers and copolymers of terpenes includes low molecular weight saturated or unsaturated polymers and copolymers of terpenes. These polymers and copolymers of terpenes may be preferably selected from α- and β-pinene copolymers, chemically modified terpenes such as terpenoids, rosins, rosin esters, terpene polyamides, styrenated terpenes, terpene phenolics, phenol-modified copolymer of styrene and alpha methyl styrene with terpenes.

The mean particle size of the microcapsules for formulating the composition of the present invention typically varies from about one tenth of a micron up to about two hundred microns in average diameter, preferably from about one to about fifty microns, and more preferably from about two microns to about 10 microns. It should be understood however that the particle size distribution of the microcapsules is not of critical importance. In an embodiment, the particle size of the encapsulated clomazone formulation of the present invention varied from about 3 microns to about 25 microns.

The homogenous dispersion of polymer microencapsulated clomazone in water with an effective emulsifier, such as lignosulfonate prepared in the first step, may be blended with a suspension system. The suspension system composition may comprise a combination of agents, such as surfactants, dispersants, antifreeze agents, clays, water, salts, polymers, and other suspension stabilizing and density balancing agents, appropriately selected to keep the microcapsules in stable homogeneous suspension in the water-based carrier over an extended period of time as long as for example two years or more.

It was further found that the desired particle size of the microcapsules could be regulated by varying the emulsification speed. It was expectedly found that smaller microcapsules afforded a faster release while larger microcapsules afforded a slower release of clomazone.

A wide range of such agents may be used, and the optimum combination for each particular suspension system of active ingredient may vary. Suitable clays include bentonite clay and attapulgite clay and mixtures thereof. The presence of at least one clay conventionally used in suspension systems improves the stability of the suspended microcapsules and particularly aids in the redistribution of the microcapsules upon shaking in the event some settling of microcapsules is experienced and redistribution thereof is required.

In an embodiment, viscosity enhancing agents may be selected from methylcellulose, ethyl cellulose, carboxymethyl cellulose, carbopol apart from xanthan gum described hereinabove. In a preferred embodiment of any process according to the present invention described herein, the viscosity modifier may be preferably added subsequent to the neutralizing step so as to ease the mixing during emulsification.

The invention further relates to a method for controlling weeds at a locus by applying to the locus of the weeds a herbicidally effective amount of a microencapsulated clomazone according to the present invention or a capsule suspension formulation obtainable by the process of the present invention.

Preferably, the present invention provides a method for controlling undesirable plant species which comprises applying to the foliage of the plants or to the soil or water containing seeds or other propagating organs thereof, a herbicidally effective amount of a microencapsulated clomazone of the present invention or a capsule suspension formulation obtainable by the process of the present invention. Preferably, the method of the present invention comprises applying to a field having a crop sown therein a herbicidally effective amount of a microencapsulated clomazone formulation of the present invention.

In an embodiment, the preferred crop may be selected from cotton, rice, wheat, soybean, tobacco, sweet potato, fruiting vegetables, cucurbit vegetables, succulent peas and bins, cole crops and tomato.

In a preferred embodiment, the preferred crop is rice. In this embodiment, a herbicidally effective amount of microencapsulated clomazone formulation is about 1 to 3 pints of the preferred formulation per acre of the field containing rice crop.

Advantageously, the microcapsule formulations prepared according to, the present invention or obtainable by the process of the present invention may be used directly as herbicidal compositions or may be diluted with water for use.

Alternatively, additional ingredients such as anti-settling agents, pH-adjusters, anti-freeze agents and the like may be added to the microcapsule compositions prepared by the process of the present invention to form concentrated microcapsule herbicidal compositions without departing from the scope of the present invention.

The invention shall now be described with reference to the following specific examples. It should be noted that the example(s) appended below illustrate rather than limit the invention, and that those skilled in the art will be able to design many alternative embodiments without departing from the scope of the present invention.

EXAMPLE 1

An organic phase was prepared with clomazone active ingredient, polymethylene polyphenylisocyanate and epoxidized soybean oil. An aqueous solution was prepared by adding lignosulfonate surfactant in required quantities in water. The organic phase and the aqueous solution were mixed together to form an emulsion. Thereafter, diethylenetriamine was added to the emulsion to allow the added diethylenetriamine to polymerize with the isocyanate crosslinker to form microcapsules that encapsulate clomazone mixed in the selected epoxidized soybean oil. After a reaction time of about 1 hour, the solution was then neutralized with hydrochloric acid to afford the following composition:

| | |
|---|---|
| Clomazone technical | 32.19 |
| Water | 34.38 |
| Lignosulfonate surfactant | 1.44 |
| DETA | 4.12 |
| Hydrochloric acid | 0.85 |

| | |
|---|---|
| Epoxidized soybean oil | 8.05 |
| Inorganic salt | 10.97 |

EXAMPLE 2

An organic phase was prepared with clomazone active ingredient, polymethylene polyphenylisocyanate and pinene polymer (20% of the organic phase) to prepare a capsule representing 6% of the total capsule weight. An aqueous solution was prepared by adding a lignosulfonate surfactant in required quantity in water. The organic phase and the aqueous solution were mixed together to form an emulsion. Thereafter, diethylenetriamine was added to the emulsion to allow the added diethylenetriamine to polymerize with the isocyanate crosslinker to form microcapsules that encapsulate clomazone mixed in the pinene polymer. Thereafter, antifoam, polyvinyl alcohol and xanthan gum may be optionally added.

| | |
|---|---|
| Clomazone technical | 32.13 |
| Calcium chloride | 10.50 |
| Water | 40.54 |
| Piccolyte AO Plus | 8.032 |
| Voranate M 220 | 2.046 |
| DETA | 1.035 |
| Propylene glycol | 3.00 |
| Other ingredients | 2.71 |

EXAMPLE 3

The following comparative formulation was prepared under the process described in example 2. An organic phase was prepared with clomazone active ingredient, polymethylene polyphenylisocyanate to prepare a capsule representing 20% of the total capsule weight. No pinene polymer was used in this formulation.

| | |
|---|---|
| Clomazone (96.8%) | 32.13 |
| Voranate M 220 | 6.411 |
| Piccolyte AO Plus | 0.000 |
| Kelig 100 | 2.500 |
| Calcium chloride | 8.000 |
| Water | 38.43 |
| Ethylene glycol | 5.000 |
| DETA | 3.242 |
| Other ingredients | 4.290 |

Effect of Pinene Polymer on the Release Rate in Air

The release rate after 12 hours in air at 50° C. for the formulation described in Example 2 represented 8.7% of the active ingredient. Example 3, which had a much larger amount of polymeric wall (20% of the organic phase is polymer wall) but had no pinene polymer present in the organic phase, had a clomazone release rate after 12 hours in air at 50° C. of 45.07%. It was thus found that increasing the wall thickness was not sufficient to limit the volatility of clomazone. It was further surprisingly found that the addition of a terpene polymer such as a pinene polymer or an epoxidized fatty acid or ester thereof was critical to reduce volatilization of the active ingredient.

Free Active Content in Water

It is believed that an increased amount of clomazone in the aqueous phase could be attributed to an increased "burst effect" administration of clomazone thereby aggravating the risk of plant phytotoxicity and off-target injury due to the volatility of the free clomazone. Thus, the free active content (in water) of the formulations according to the present invention e.g. the formulation of example 1 above was compared to the free active content of a comparable strength and commercially available encapsulated formulation. The method for measuring the free active content release into water was as follows:

0.25 g of each formulation was dispersed in 70 g (70 ml) of water, mixed for 2 minutes with a magnetic stir bar, filtered under vacuum through a Buchner funnel (with a 0.7 μm GFC Whatman filter, 9 cm diameter), washed with 60 g (60 ml) water, and extracted in a separatory funnel with 26.5 g (40 ml) hexane. The organic phase was collected and 1 microliter was injected onto the GC column. The results are reported in the table 2 below. The free active ingredient measured in the aqueous phase is reported in % of free active ingredient compare to the total amount of active ingredient present in the formulation.

TABLE 2

| Formulation | Free active content (%) of total content in formulation |
|---|---|
| 360 ME commercial formulation | 0.98% |
| Example 1 | 0.50% |

It was thus found that the presence of an epoxidized vegetable oil substantially improved the encapsulation of the active ingredient according to the present invention, which was reflected in the reduced quantity of the active ingredient measured in the aqueous phase.

Volatility Reduction

A field trial was conducted in spring wheat on a Harriston loam soil having pH 7.7. The treatments were assigned to 38.1 cm (15") wide by 8 m long crop bare plots separated by 15' planter width strips of spring wheat (24 rows spaced 7.5" apart). The plants were replicated 4 times and arranged according to a randomized complete block design. The plots were either bare soil or covered in weeds, primarily sow thistle and vetch. Treatments were applied using a $CO_2$ powered backpack sprayer fitted with a single Teejet 8002 brass nozzle calibrated to deliver 339.3 L/ha (36.3 US gal/ac) of water. The soil was moist at time of application because of supplemental wetting (applied water) on replicates 3 and 4. The temperature was 18-22° C., humidity was moderate and there was no wind during application. The treatments were evaluated for volatility effects on adjacent wheat rows by estimating rows bleached or dead on either side of the treatment strip on days 1, 3, 6, 10, 14, 21 and 34 after treatment (DAT). Plots were also rated according to a 1-9 scale (rating scale appears below).

Ratings Scale:
1: No damage
2—slight bleaching, no height reduction
3—slight height reduction with more bleaching
4—1 to 2 rows dead with some bleaching
5—1 to 2 rows dead with more bleaching
6—2 to 3 rows dead with some bleaching
7—2 to 3 rows dead with more bleaching
8—4 to 5 rows dead with bleaching throughout the plot
9—all plants dead Results: Data are presented in Table 3. At 1 DAT minimal initial bleaching was seen on newest wheat growth on wheat adjacent to treatments. At 3 DAT all small wheat was similarly affected by clomazone volatility by bleaching symptoms on newest 2-3 wheat leaves and treatment differences were not obvious. The volatility damage was much the same at the 6 DAT assessment compared to the 3 DAT rating. At 10 DAT the wheat adjacent to the control plots in the small wheat became remarkable because of a slightly greener tinge to the crop canopy indicating the crops in these plots recovered from the bleaching damage. By 14 DAT the small wheat outgrew the bleaching damage in the treated plots. The wheat rows in the untreated plots greened up across the full seeder width (24 rows). Most of the wheat continued to recover as the season progressed (21, 34 and 64 DAT), but heavily damaged rows closest to the treated plots either died or showed reduced recovery. There was significant difference in volatility damage between the tested formulations.

TABLE 3

| Treatment | Rate (kg a.i./Ha) | Day 3 (Average number of rows effected) | Day 6 (Average number of rows effected) | Day 10 (Average number of rows effected) |
|---|---|---|---|---|
| Example 1 | 16.8 | 3.90 | 4.50 | 3.50 |
| Commercial CS 360 g/L | 16.8 | 8.50 | 9.80 | 8.00 |
| EC 360 g/L | 16.8 | 11.30 | 12.50 | 11.30 |

The data presented in table 3 above clearly shows that there was a substantial reduction in the number of rows of wheat affected initially with the application of the present formulation over the conventionally known formulation, which reflected the reduced volatility of the formulations according to the present invention.

In the same experimental setting, the average number of rows of small wheat plants which were found dead and the average number of rows bleached in small wheat was also measured, which results are summarized in table 4 appearing hereinafter.

TABLE 4

| Treatment | Rate (kg a.i./Ha) | Average number of rows dead in small wheat | Average number of rows bleached in small wheat | Phytotoxicity ratings |
|---|---|---|---|---|
| Example 1 | 16.8 | 1.75 | 7.13 | 3.60 |
| Commercial CS 360 g/L | 16.8 | 2.25 | 15.50 | 5.0 |

It was found that there was 54% reduction in the average number of rows bleached in small wheat and 28.5% reduction in the number of dead small wheat plants, which was considered a surprising indication of the substantially reduced volatility of the formulations of the present invention. It was found that the formulation of Example 1 only caused a slight height reduction in the affected plants while at least two rows were found dead with the commercial 360 g/L CS formulation.

Without wishing to be bound by theory, it is believed that the presence of a stabilizing effective amount of epoxidized fatty esters such as epoxidized oleochemicals substantially enhanced the plasticity of the polymeric shell wall thereby preventing the rapid diffusion of the active ingredient clomazone and rupture of the polymeric shell wall.

Reduced Phytotoxicity

In an experimental set up, square plots with 50 foot sides were set up. A 0.5-1.0 m diameter circle was designated as the target application area in each plot. The designated target application areas were handweeded to remove all the green plant material. This area was watered with approximately 0.1-0.2 inches of water within an hour of the application of the test formulations to ensure that the applications were made to a wet, bare soil surface. A plastic barrier was placed with no bottom or top was placed vertically on the target application area prior to the formulation applications.

The applications were made with the wind speeds were within 5 mph. Spray solutions containing the test formulations were prepared by diluting the test formulations with water to an equivalent of 220 gallons of water per acre and applied to the target application areas. The spray solutions were applied inside the plastic barriers, which were removed 1-2 minutes subsequent to the application to ensure that the spray droplets settle to the ground.

Phytotoxic evaluations were collected at 1, 3, 7, 14 and 21 days after the application of the test formulations. The measurements were taken from the outer edge of the application sites to the location of the plants furthest away from the edge of the application site which were observed to exhibit phytotoxic symptoms. The phytotoxic symptoms evaluated were whitening for tomato or its plant weight and bleaching for spring wheat crop. The phytotoxic results were tabulated as hereunder:

TABLE 5

|  | 1 DAT (% injury) | 3 DAT (% injury) | 7 DAT (% injury) | 14 DAT (% injury) | 21 DAT (% injury) |
|---|---|---|---|---|---|
| Rating Distance 0-6 INCH ||||||
| Example 1 | 0 | 0.5 | 7.3 | 33.8 | 35 |
| Commercial formulation | 0.5 | 0.5 | 16.3 | 38.8 | 43.8 |
| Rating Distance 6-12 INCH ||||||
| Example 1 |  | 0 | 3.0 | 15 | 20 |
| Commercial formulation |  | 0 | 6.3 | 27.5 | 27.5 |
| Rating Distance 12-18(24) INCH ||||||
| Example 1 |  |  | 0 | 2.5 | 0.8 |
| Commercial Formulation |  |  | 0 | 7.3 | 2.0 |

It was surprisingly found that the formulation of Example 1 exhibited consistently lower amount of injury (bleaching of leaves) observed that each distance parameter when compared to the commercial 360 g/L CS formulation. Unexpectedly, the formulation of example 1 always exhibited less injury than the commercial 360 g/L CS formulation regardless of the distance from the site or the time of evaluation. Moreover, injury symptoms (<5%) to wheat were seen from commercial 360 g/L CS formulation treatment at the initial 1 and 3 days after application evaluation but surprisingly no such injury was with the formulation of Example 1 treatment.

A similar protocol was adopted for the comparison of phytotoxicity (measured by tomato whitening) on big red tomato variety.

TABLE 6

| S No. | Dosage | Percentage whitening 16 DAT Crop 1 | Percentage whitening 29 DAT Crop 1 | Percentage whitening 29 DAT Crop 2 | Average plant weight in grams on 30 DAT |
|---|---|---|---|---|---|
| Formulation of Example 1 | 2.25 pt/a | 18.3 | 6.7 | 0.0 | 27.513 |
| Commercial 360 g/L CS | 2.25 pt/a | 33.0 | 25.0 | 16.7 | 11.390 |

It was surprisingly found that the formulation of Example 1 exhibited significantly lower whitening in big red tomato vis-à-vis the commercial formulation. It was further surprisingly that the Example 1 formulation did not stunt the growth of the big red tomato species i.e. higher plant weight on comparison vis-à-vis the commercial 360 g/L formulation.

It was thus concluded that the extent of bleaching seen with the formulation of Example 1 was substantially lesser than the extent of bleaching seen with the commercial formulation.

Further Advantage of One or More Embodiments of the Present Invention

It was found that an improper addition of the stabilizers and surfactants in a manner other than hereinabove described provided an organic phase external to the microcapsules wherein the added clomazone active ingredient was soluble. The presence of this external organic environment extracted clomazone from within the microcapsules thereby increasing the volatility of the resulting formulation to a level similar to an unencapsulated formulation.

It has also been found that by encapsulating clomazone dissolved in a suitable water-immiscible adjuvant selected from epoxidized derivatives of fatty acids or esters thereof and polymers and copolymers of terpenes such as described herein, clomazone may be surface-applied directly by spraying. It was then possible to achieve effective weed control in crops without significant damage to neighboring unsprayed vegetation due to vapor transfer of the herbicide.

It has further been found that the formulations according to the present invention exhibit significant bioefficacy for the control of undesired weeds, which is maintained throughout the shelf life of the formulations.

Wherein the foregoing reference has been made to components having known equivalents, then such equivalents are herein incorporated as if individually set forth. Accordingly, it will be appreciated that changes may be made to the above described aspects and embodiments of the invention without departing from the principles taught herein. Additional advantages of the present invention will become apparent for those skilled in the art after considering the principles in particular form as discussed and illustrated. Thus, it will be understood that the invention is not limited to the particular embodiments described or illustrated, but is intended to cover all alterations or modifications which are within the scope of the described invention.

The invention claimed is:

1. A storage stable capsule suspension formulation comprising a herbicidally effective amount of clomazone encapsulated within a polymeric shell wall of microcapsules, said microcapsules characterized in comprising a stabilizing effective amount of polymers and copolymers of terpenes.

2. The formulation as claimed in claim 1, wherein said polymeric shell wall is formed by condensation of at least one wall forming component.

3. The formulation as claimed in claim 1, wherein said polymeric shell wall is formed by self-condensation of a wall forming component.

4. The formulation as claimed in claim 1, wherein said polymeric shell wall is formed by interfacial condensation of a first and a second wall forming components, each being included separately in at least two immiscible liquids.

5. The formulation as claimed in claim 4, wherein said immiscible liquids are an organic phase and an aqueous phase.

6. The formulation as claimed in claim 5, wherein said polymers and copolymers of terpenes comprises up to about 70% by weight of the organic phase.

7. The formulation as claimed in claim 1 wherein the polymeric shell wall constitutes from about 20% by weight to about 40% by weight of the organic phase.

8. The formulation as claimed in claim 5, wherein said organic phase is dispersed in the aqueous phase.

9. The formulation as claimed in claim 6, wherein the particle size of the dispersed organic phase is from about 0.1 microns to about 200 microns.

10. The formulation as claimed in claim 9, wherein said polymeric shell wall material is polyurea.

11. The formulation as claimed in claim 1, wherein said polymers and copolymers of terpenes are selected from pinene homopolymers, pinene copolymers selected from α- and β-pinene copolymers, polyterpene oligomers, terpenoid, rosin, rosin ester, terpene polyamide, styrenated terpene, terpene phenolic, and phenol-modified copolymer of styrene and alpha methyl styrene with terpene.

12. The formulation as claimed in claim 1 additionally comprising at least one ingredient selected from a plasticizer, a tackifier, an antifoam, a rheology modifier, a density modifier; a neutralizing acid, a biocide and a film forming agent.

13. The formulation as claimed in claim 1, wherein said polymeric shell wall material is selected from polyurea, polyurethane, polyamide, polycarbonate, polysulfonamide, urea formaldehyde, melamine resin, melamine urea resin, gelatin, gum arabic shell wall, crosslinked and non-crosslinked combinations thereof.

14. The formulation as claimed in claim 1, wherein said formulation additionally comprises a surfactant selected from ethoxylated lignosulfonic acid salt, lignosulfonic acid salt, oxidized lignin, lignin salt, salt of styrene-maleic anhydride copolymer, polyvinyl alcohol, salt of partial esters of styrene-maleic anhydride copolymer, partial salt of polyacrylic acid and partial salt of polyacrylic acid terpolymers.

15. The formulation as claimed in claim 1 comprising from about 10% to about 50% of clomazone active ingredient.

* * * * *